United States Patent [19]

Osterman et al.

[11] Patent Number: 5,084,625
[45] Date of Patent: Jan. 28, 1992

[54] APPARATUS FOR TRANSPORTING HAZARDOUS MATERIALS

[75] Inventors: Robert A. Osterman, Canonsburg; Robert Cox, West Mifflin, both of Pa.

[73] Assignee: United States Department of Energy, Washington, D.C.

[21] Appl. No.: 644,050

[22] Filed: Jan. 22, 1991

[51] Int. Cl.⁵ ............................................. G21F 5/02
[52] U.S. Cl. ........................... 250/506.1; 250/507.1; 250/496.1
[58] Field of Search ............... 250/506.1, 507.1, 505.1, 250/496.1, 497.1; 414/217

[56] References Cited

U.S. PATENT DOCUMENTS

| | | | |
|---|---|---|---|
| 2,810,839 | 10/1957 | Ferguson | 250/496.1 |
| 2,889,464 | 6/1959 | Ruehle, Jr. | 250/106 |
| 3,852,599 | 12/1974 | Smith | 250/328 |
| 4,066,909 | 1/1977 | Bourdois et al. | 250/497 |
| 4,513,204 | 4/1985 | Domnanovich et al. | 250/496.1 |
| 4,532,816 | 8/1985 | Miller | 73/864.91 |
| 5,035,342 | 7/1991 | Houghton | 250/506.1 |

Primary Examiner—Jack I. Berman
Assistant Examiner—Kiet T. Nguyen
Attorney, Agent, or Firm—Judy K. Kosovich; William R. Moser; Richard E. Constant

[57] ABSTRACT

An apparatus and method are provided for selectively receiving, transporting, and releasing one or more radioactive or other hazardous samples for analysis on a differential thermal analysis (DTA) apparatus. The apparatus includes a portable sample transporting apparatus for storing and transporting the samples and includes a support assembly for supporting the transporting apparatus when a sample is transferred to the DTA apparatus. The transporting apparatus includes a storage member which includes a plurality of storage chambers arrayed circumferentially with respect to a central axis. An adjustable top door is located on the top side of the storage member, and the top door includes a channel capable of being selectively placed in registration with the respective storage chambers thereby permitting the samples to selectively enter the respective storage chambers. The top door, when closed, isolates the respective samples within the storage chambers. A plurality of spring-biased bottom doors are located on the bottom sides of the respective storage chambers. The bottom doors isolate the samples in the respective storage chambers when the bottom doors are in the closed position. The bottom doors permit the samples to leave the respective storage chambers from the bottom side when the respective bottom doors are in respective open positions. The bottom doors permit the samples to be loaded into the respective storage chambers after the analysis for storage and transport to a permanent storage location.

18 Claims, 4 Drawing Sheets

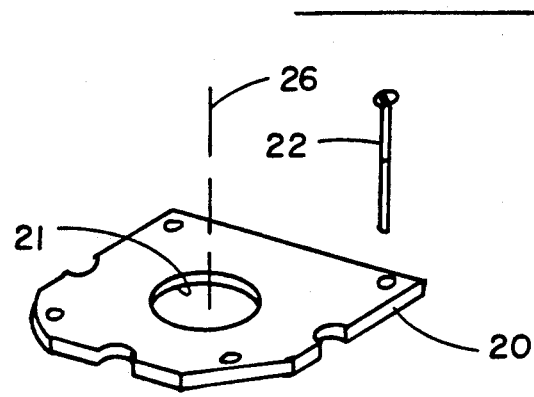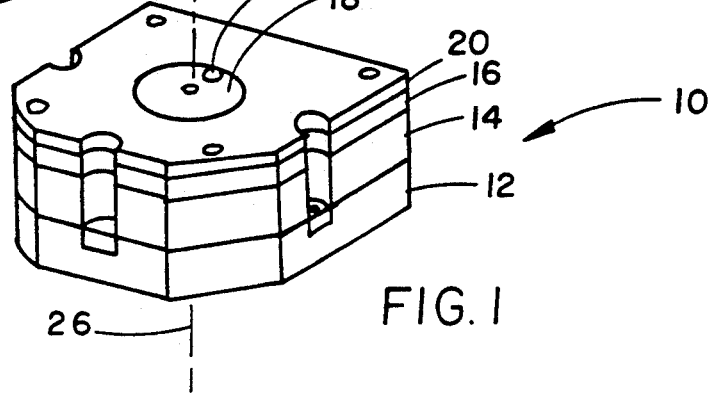
FIG. 2
FIG. 1

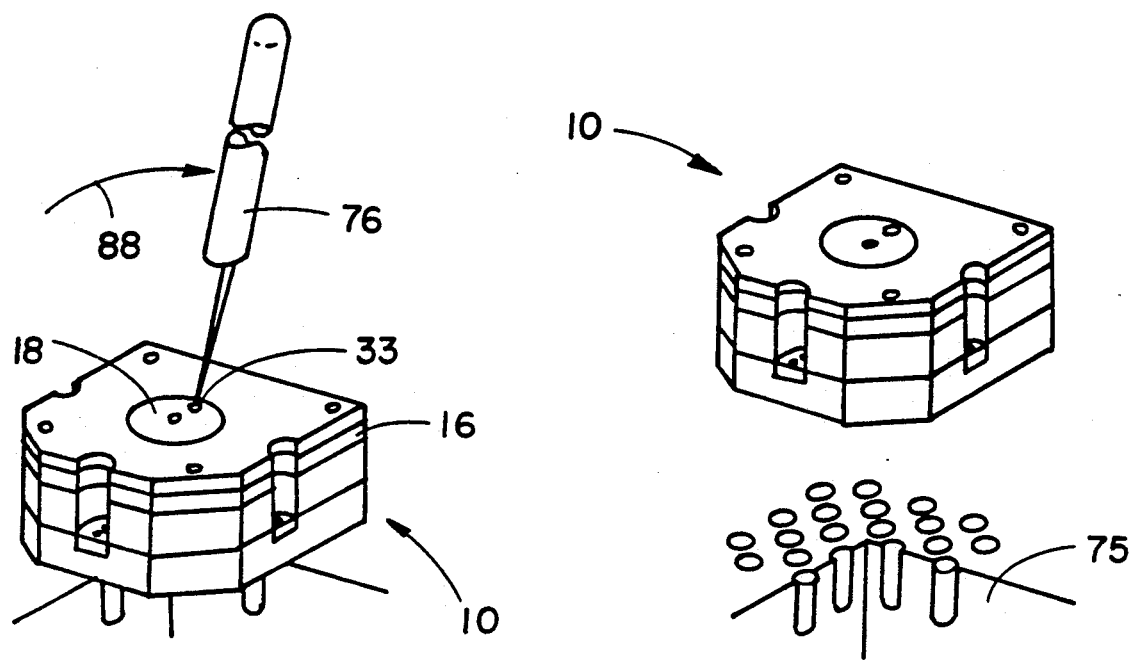
FIG. 8
FIG. 9
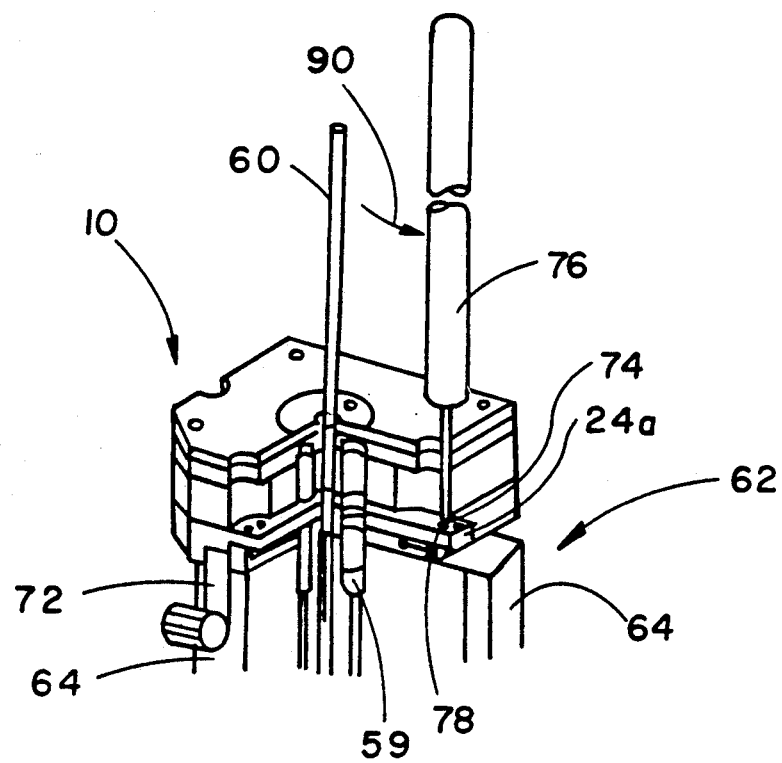
FIG. 10

APPARATUS FOR TRANSPORTING HAZARDOUS MATERIALS

The United States Government has rights in this invention pursuant to Contract No. DE-AC11-76PN00014 between the United States Department of Energy and Westinghouse Electric Corporation.

BACKGROUND OF THE INVENTION

The present invention relates to the field of transporting hazardous materials, especially radioactive materials, to an apparatus for measuring and testing, especially an apparatus for differential thermal analysis.

Radioactive materials are often handled in a containment area such as a glovebox. However, apparatus for analyzing radioactive materials is often located outside of the containment area. For example, a sample of radioactive material may be taken in a glovebox for analysis in a differential thermal analyzer located outside the glovebox.

More specifically, a standard commercial differential thermal analysis (DTA) apparatus would be extremely difficult, if not impossible, to operate inside a glovebox due to the fact that the DTA apparatus components are extremely fragile. Moreover, milligram quantities of the sample material must be handled with a precision that is extremely difficult and time consuming to perform within the confines of a containment device such as a glovebox. Furthermore, proper maintenance of a DTA apparatus would be difficult inside a glovebox. In addition, a furnace for DTA may routinely operate at 1,000 degrees Centigrade, thereby making it economically unfeasible to adequately cool the glovebox to within current specifications for proper fire prevention.

In analyzing a radioactive sample in an apparatus outside a glovebox, it is desirable that the radioactive sample does not come into contact with either personnel or the environment outside the analytical apparatus. More specifically it is desirable that a radioactive sample remain untouched by personnel and isolated from the environment as the sample is taken, as the sample is loaded into a sample transporter in a glovebox, as the sample is transported to an analytical apparatus, as the sample is analyzed and as the analyzed sample is returned to the glovebox.

SUMMARY OF THE INVENTION

Accordingly it is an object of the present invention to provide a transporting apparatus for a radioactive sample whereby the sample remains untouched after the sample is taken and loaded into the sample transporter in a glovebox, as the sample is transported to an analytical apparatus, as the sample is analyzed, and as the analyzed sample is returned to the glovebox.

Another object of the invention is to provide an apparatus that effectively contains radioactive samples that are accidentally dropped when being transported from a glovebox to a measuring or testing apparatus.

Another object is to provide a sample transporter for crucibles used in a DTA apparatus wherein the transporter accommodates different crucible sizes that are utilized by various DTA equipment.

Additional objects, advantages, and novel features of the invention will be set forth in part in the description that follows and in part will become apparent to those skilled in the art upon examination of the following or may be learned with the practice of the invention. The objects and advantages of the invention may be realized and attained by means of the instrumentalities and combinations particularly pointed out in the appended claims.

To achieve the foregoing and other objects, and in accordance with the purposes of the present invention as described herein, an improved apparatus and method are provided for selectively receiving, transporting, and releasing a hazardous sample for analysis on an analytical apparatus. The subject apparatus includes a portable storage member for storing and transporting the sample. The storage member includes a top side and a bottom side. An adjustable top door is located on the top side of the storage member, and the top door permits the sample to enter the storage member through the top side when the top door is in an open position. The top door isolates the sample within the storage member when the top door is in a closed position. An adjustable bottom door is located on the bottom side of the storage member. The bottom door isolates the sample in the storage member when the bottom door is in the closed position and the bottom door permits the sample to leave the storage member through the bottom side when the bottom door is in the open position.

More specifically, the storage member includes a plurality of storage chambers arrayed circumferentially with respect to a central axis. An adjustable top door is located on the top side of the storage member, and the top door includes a channel capable of being selectively placed in registration with the respective storage chambers thereby permitting the samples to selectively enter the respective storage chambers through the top side when the top door is in an open position. The top door isolates the respective samples within the storage chambers by placing the top door channel out of registration with the respective storage chambers when the top door is in a closed position.

In addition, a plurality of adjustable bottom doors are located on the bottom sides of the respective storage chambers. The bottom doors isolate the samples in the respective storage chambers when the bottom doors are respectively in the closed position. The bottom doors permit the samples to leave the respective storage chambers from the bottom side when the respective bottom doors are in respective open positions. The bottom doors are supported by a base member that is located below and supports the storage member.

Preferably, the bottom doors include springs for biasing the doors in the closed position. The bottom doors also include actuator means for engaging a hand-held implement for opening the doors.

The apparatus of the invention can be especially adapted for use with a DTA apparatus. In this respect, the apparatus further includes a channel for receiving a sparge tube of the DTA apparatus.

For use with a DTA apparatus, the apparatus of the invention further includes a support for supporting the sample transporter so that the sample transporter is properly positioned with respect to the sample receiving portion of the DTA apparatus. To facilitate alignment of the sample transporter with the DTA apparatus, a lock is provided to lock the two elements together.

In accordance with another aspect of the invention, a method of handling hazardous analytical samples is provided. In the method, a plurality of sample containers are first loaded into a plurality of storage chambers of a portable transporter in a containment area. The transporter serves to isolate the sample containers from the environment. The transporter containing the sample containers are then transported to an analytical apparatus, such as a DTA apparatus. The transporter is placed in close proximity to a sample receiving portion of the analytical apparatus, such that a sample container is permitted to move directly from a storage chamber in the transporter to the receiving portion of the analytical apparatus. The transporter is then moved away from the analytical apparatus. After an analysis is performed, the transporter is once again placed in close proximity to the sample receiving portion of the analytical apparatus. The sample container is then moved from the analytical apparatus directly into a storage chamber in the transporter, and the sample container is isolated from the environment by being in the storage chamber.

Still other objects of the present invention will become readily apparent to those skilled in this art from the following description, wherein there is shown and described a preferred embodiment of this invention. Simply by way of illustration, the invention will be set forth in part in the description that follows and in part will become apparent to those skilled in the art upon examination of the following or may be learned with the practice of the invention. Accordingly, the drawings and descriptions will be regarded as illustrative in nature and not as restrictive.

BRIEF DESCRIPTION OF THE DRAWINGS

The accompanying drawings incorporated in and forming a part of the specification, illustrate several aspects of the present invention, and together with the description serve to explain the principles of the invention. In the drawings:

FIG. 1 is a perspective view of an embodiment of a sample container transporting apparatus of the invention;

FIG. 2 is an exploded view of the sample transporting apparatus shown in FIG. 1;

FIGS. 4–10 show the sequence of steps for loading sample containers into the transporter, for transporting the samples, and for unloading the samples into the DTA apparatus.

DETAILED DESCRIPTION

Figure 3:
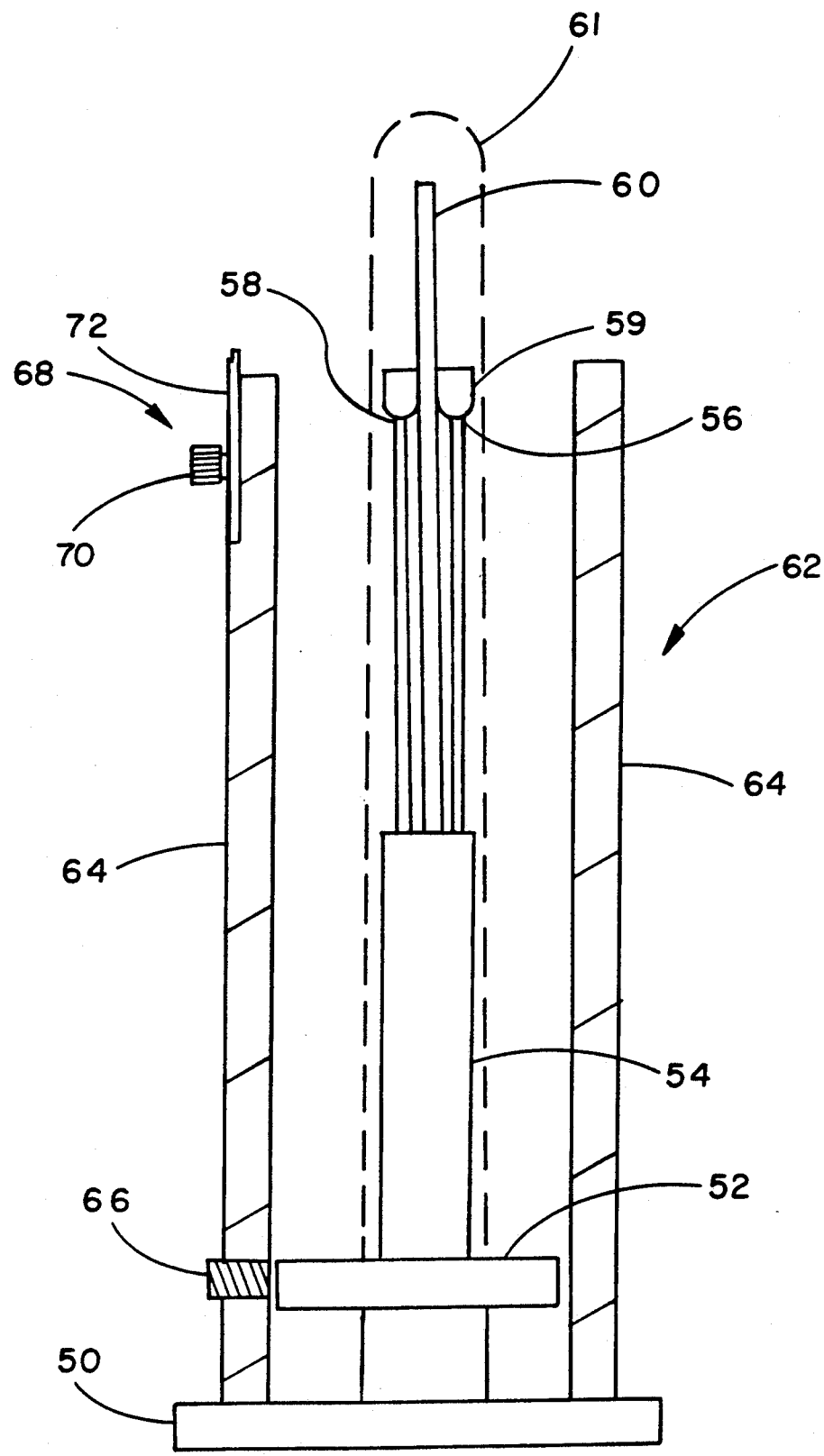
FIG. 3 is a schematic view of a DTA apparatus used in conjunction with a support for the transporter shown in FIG. 1.

Referring to FIGS. 1 and 2, the sample transporting apparatus 10 of the invention includes a bottom base portion 12, a middle storage chamber element 14, an intermediate element 16, a rotatable door 18, and a top element 20. The rotatable door 18 has a flange 19 the engages a complementary flange 21 in the top element 20. The interengaging flanges 19 and 21 facilitate rotation of the door 18 and maintain proper alignment of the door 18. Screws 22 are provided for fastening elements 12, 14, 16, and 20 together. Door 18 is freely rotatable when the apparatus 10 is fully assembled as shown in FIG. 1.

Three bottom doors 24 are present in base portion 12. The bottom doors 24 are arrayed circumferentially around vertical axis 26.

Registerable sample channels are present in most of the elements composing the transporter 10 of the invention. More specifically, base portion 12 has three sample channels 28 placed directly below the respective bottom doors 24. Middle storage chamber element 14 has three sample channels 30. Intermediate element 16 has three sample channels 32. The rotatable door 18 has one sample channel 33.

Each bottom door 24 includes a spring 34 for biasing the door in the closed position. Each bottom door 24 also includes a stop member 36 for exerting a compressive force against one end of the spring 34 when the bottom door 24 is opened. The other end of the spring 34 is in contact with an inner wall 25 of the base portion 12. When the stop member 36 contacts the inner wall 25, the stop member 36 prevents the door 24 from moving more than a predetermined distance when closing. Both the stop member 36 and the spring 34 are located in a groove 27 located in the base portion 12. When the bottom door 24 is fully closed, the stop member 36 comes into contact with an inner wall of the groove 27. When the bottom door 24 is opened, the stop member 36 moves toward an outer wall of the groove 27 as the stop member 36 compresses the spring 34.

Coaxial with the vertical axis 26, respective sparge tube channels are present in most of the elements of the transporter 10. More specifically, a sparge tube channel 38 (see cross-section in FIG. 5) is present in base portion, 12. A sparge tube channel 40 is present in middle storage chamber element 14. A sparge tube channel 42 is present in intermediate element 16. And a sparge tube channel 46 is present in top door 18.

In FIG. 3, a DTA apparatus includes a base 50, a furnace tube nut assembly 52, a thermocouple support 54, a thermocouple position point 56, crucible holders 58 and 59, a sparge tube 60, and a furnace tube 61.

As part of the invention, a support assembly 62 is shown for supporting the sample transporter 10 shown in FIG. 10. The support assembly 62 includes support members 64 which may be walls, struts, legs, or the like. Means (not shown) are provided for joining the support members 64 together to form a stable support assembly 62. A set screw 66 is located in one of the support members 64. By turning the set screw 66, the set screw 66 contacts the furnace tube nut assembly 52 such that the support assembly 62 is stabilized with respect to the DTA apparatus.

A lock assembly 68 is located near the top of one of the support members 64. The lock assembly 68 includes a thumb screw 70 and a locking bar 72. When the transporting apparatus 10 of the invention is placed on the support assembly 62, the lock assembly 68 is used to fix the transporting apparatus 10 and the support assembly 62 together. The lock assembly 68 is unlocked to remove the transporting apparatus 10 away from the support assembly 62.

The operation of the invention is described with reference to FIGS. 4–10. For radioactive samples located in a containment the transporting apparatus 10 are shown in FIGS. 4–9. The step of unloading the transporting apparatus 10 is shown in FIG. 10.

Figure 4:
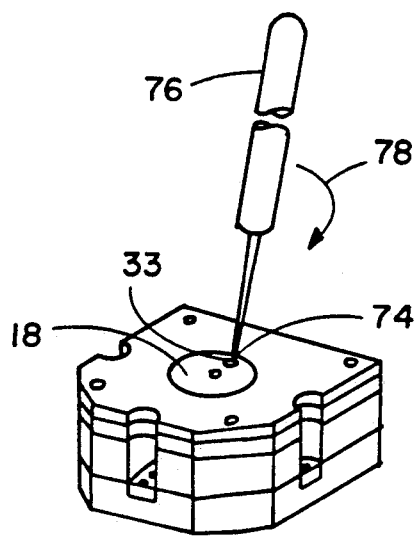

In FIG. 4, a tip 74 of a hand-held scribe 76 is placed in the sample channel 33 of the top door 18. The door 18 is rotated clockwise as shown by arrow 78 until the sample channel 33 is in registration with other sample channels 28, 30, 32 as shown in FIG. 5.

Figure 5:
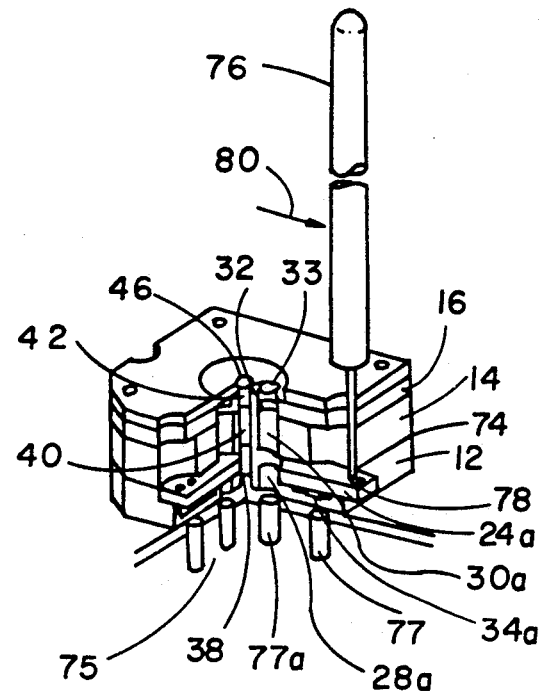

In FIG. 5, the transporting apparatus 10 has been placed adjacent to a tray 75 holding a plurality of sample containers 77 which are DTA apparatus crucibles. The channel 28a of the base portion 12 is in registration with crucible 77a in the tray 75. The tip 74 of the scribe 76 is placed in an opening 78 in bottom door 24a. By pushing the scribe 76 in the direction of arrow 80, the bottom door 24a is moved against spring 34a so that there is an open passage between channel 28a and channel 30a. Therefore, with the door 24a open, there is a continuous passageway from the top of the transporting apparatus 10 to the crucible 77a.

Figure 6:
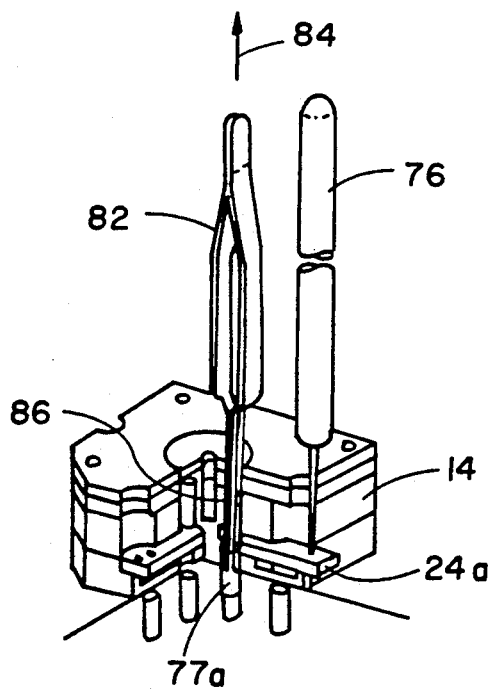

As shown in FIG. 6, as the bottom door 24a is kept open by the scribe 76, a reverse action tweezers 82 is used to retrieve the crucible 77a into the transporting apparatus 10. The crucible 77a is pulled up in the direction of arrow 84 into storage chamber 86 in the middle storage chamber element 14.

Figure 7:
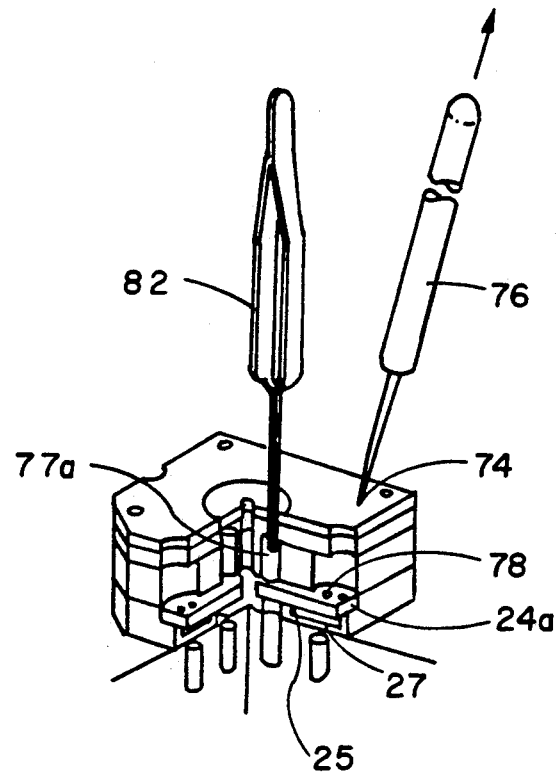

Then, as shown in FIG. 7, the tip 74 of the scribe 76 is removed from the opening 78, and the bottom door 24a closes by force of compressed spring 34a. With the bottom door 24a closed, the crucible 77a is retained in the storage chamber 86.

As shown in FIG. 8, the scribe 76 is used to rotate the top door 18 in the direction of the arrow 88 so that the sample channel 33 of the top door 18 is no longer in registration with the sample channel 32 of the intermediate element 16. In this way, the crucible 77a is contained in the transporting apparatus 10 and is isolated from the environment surrounding the apparatus 10.

As shown in FIG. 9, the transporting apparatus 10 containing the environmentally-isolated crucible 77a is lifted away from the tray 75. Then the transporting apparatus 10 is transported out of the radioactive or hazardous materials containment areas and brought to the DTA apparatus shown in FIG. 3.

As shown in FIG. 10, the transporting apparatus 10 has been placed on support members 64 of the support assembly 62 (see FIG. 3 for more details). The locking bar 72 is in locking engagement with the transporting apparatus 10, and sparge tube 60 is projecting up through the passageway formed by the sparge tube channels in the transporting apparatus 10. In FIG. 10, the tip 74 of the scribe 76 has been placed in opening 78 of the bottom door 24a and has been pushed in the direction shown by arrow 90. In this way, door 24a is opened, and crucible 77a drops under the influence of gravity out of the transporting apparatus 10 into crucible holder 59.

After the crucible 77a drops out of the transporting apparatus 10, the scribe 76 is removed from the apparatus 10, the bottom door 24a shuts as a result of spring bias force, the locking bar 72 is disengaged from the apparatus 10, and the apparatus 10 is lifted vertically along the sparge tube 60 until the apparatus 10 clears the sparge tube 60.

After the analysis is completed, the crucible 77a is removed from DTA apparatus and loaded into the transporting apparatus 10 with tweezers 82 in a manner similar to the manner of loading the apparatus 10 in the glovebox as shown in FIGS. 4-8 discussed hereinabove. Then additional crucibles contained in the transporting apparatus 10 can be analyzed successively. After all the analyses are completed, the apparatus 10 is then transported back to the glovebox for removal of the used crucible 77a and other crucibles and possible replacement with fresh samples.

The materials of which the transporting apparatus 10 is composed may be any material capable of withstanding temperatures that may be present at the sample receiving areas of the analytical apparatus. The apparatus 10 can be lead-lined to prevent radiation from escaping from the apparatus 10 into the environment.

In summary, numerous benefits have been described which result from employing the principles of the invention. With the invention a transporting apparatus is provided for a radioactive sample (or sample of other hazardous material) whereby the sample remains untouched after the sample is taken and loaded into the sample transporter in a glovebox, as the sample is transported to an analytical apparatus, as the sample is analyzed, and as the analyzed sample is removed from the analytical apparatus and returned to the glovebox.

By employing the invention, an apparatus is provided that effectively contains radioactive or other hazardous samples that are accidentally dropped when being transported from a glovebox to a measuring or testing apparatus.

The foregoing description of the invention has been presented for purposes of illustration and description. It is not intended to be exhaustive or to limit the invention to the precise form disclosed. Obvious modifications or variations are possible in light of the above teachings. For example, the sample channels can be of different sizes to accommodate different size sample crucibles or other sample containers. The embodiment was chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

What is claimed is:

1. A portable apparatus for selectively receiving, transporting, and releasing a sample, comprising:
    a portable storage member for storing and transporting the sample, said storage member including a top side and a bottom side,
    an adjustable top door located on the top side of said storage member, said top door permitting the sample to enter said storage member through said top side when said top door is in an open position, and said top door isolating the sample within said storage member when said top door is in a closed position, and
    an adjustable bottom door located on the bottom side of said storage member, said bottom door isolating the sample in said storage member when said bottom door is in the closed position, and said bottom door permitting the sample to leave said storage member through said bottom side when said bottom door is in the open position.

2. An apparatus for selectively receiving, retaining, and releasing a sample, comprising:
    a base member including a channel permitting the sample to pass through said base member,
    an adjustable bottom door supported by said base member, said bottom door including a channel capable of permitting the sample to pass through said bottom door when said bottom door is in an open position such that said bottom door channel is in registration with said base member channel, and said bottom door capable of retaining the sample when said bottom door is in a closed position,
    a storage member supported by said base member and located above said bottom door, said storage member including a channel capable of permitting the sample to be received, to be stored when said bottom door is in the closed position, and to be released when the bottom door is in the open position, and an adjustable top door supported by said storage member, said top door including a channel capable of permitting the sample to pass into said storage member channel when said top door is in the open position such that said top door channel is in registration with said storage chamber channel, and said top door capable of isolating the sample when said top door is in the closed position.

3. A portable apparatus for selectively receiving, transporting, and releasing a plurality of samples, comprising:

a portable storage member for storing and transporting the samples, said storage member including a top side and a bottom side, said storage member including a plurality of storage chambers arrayed circumferentially with respect to a central axis, an adjustable top door located on the top side of said storage member, said top door including a channel capable of being selectively placed in registration with said respective storage chambers thereby permitting the samples to selectively enter said respective storage chambers through said top side when said top door is in an open position, and said top door isolating the respective samples within said storage chambers by placing said top door channel out of registration with said respective storage chambers when said top door is in a closed position, and a plurality of adjustable bottom doors located respectively on the bottom sides of said respective storage chambers, said bottom doors isolating the samples in said respective storage chambers when said bottom doors are respectively in the closed position, and said bottom doors permitting the samples to leave said respective storage chambers from said bottom side when said respective bottom doors are in respective open positions.

4. The apparatus described in claim 3 wherein said bottom doors are supported by a base member located below and supporting said storage member.

5. The apparatus described in claim 3 wherein said bottom doors include springs for biasing said doors in the closed position.

6. The apparatus described in claim 3 wherein said bottom doors include actuator means for engaging a hand-held implement for opening said doors.

7. The apparatus described in claim 3 wherein said bottom doors include stop means for preventing said doors moving more than a predetermined distance when closing and for compressing a door-biasing spring when opening.

8. The apparatus described in claim 3, further including a channel for receiving a sparge tube of a differential thermal analysis apparatus.

9. An apparatus for handling sample containers for a thermal analysis apparatus and for isolating the sample containers from an adjacent environment, comprising:

means for transporting a plurality of sample containers from a loading area to the thermal analysis apparatus, said transport means including a plurality of sample chambers for housing the respective sample containers, said transport means including means for isolating the sample containers from the environment and for permitting loading and unloading the sample containers respectively to and from a sample receiving portion of the thermal analysis apparatus, and means for supporting said transport means adjacent to the sample receiving portion of the thermal analysis apparatus, said support means permitting registration of said respective sample chambers with the sample receiving portion of the thermal analysis apparatus.

10. The apparatus described in claim 9 wherein:
the thermal analysis apparatus is a differential thermal analysis (DTA) apparatus, and
said transport means includes a channel adapted to receive a sparge tube of the DTA apparatus.

11. The apparatus described in claim 9 wherein said support means includes means for engaging said transport means.

12. The apparatus described in claim 9 wherein said support means includes means for locking together with said transport means.

13. The apparatus described in claim 9 wherein said support means includes means for engaging with the thermal analysis apparatus.

14. An apparatus for handling sample containers for a differential thermal analysis apparatus and for isolating the sample containers from an adjacent environment, comprising:

means for transporting a plurality of sample containers from a loading area to the differential thermal analysis apparatus, said transport means including a plurality of sample chambers for housing the respective sample containers, said transport means including a channel adapted to receive a sparge tube of the differential thermal apparatus and said transport means including means for isolating the sample containers from the environment and for permitting loading and unloading the sample containers respectively to and from a sample receiving portion of the differential thermal analysis apparatus, and means for supporting said transport means adjacent to the sample receiving portion of the differential thermal analysis apparatus, said support means including means for engaging with said transport means said support means permitting registration of said respective sample chambers with the sample receiving portion of the differential thermal analysis apparatus.

15. The apparatus described in claim 14 wherein said support means includes means for engaging said transport means.

16. The apparatus described in claim 14 wherein said support means includes means for locking together with said transport means.

17. The apparatus described in claim 14 wherein said support means includes means for engaging with the differential thermal analysis apparatus.

18. A method of handling hazardous analytical samples, comprising the steps of:
loading a plurality of sample containers into a plurality of storage chambers of a portable transporter in a containment area, the transporter serving to isolate the sample containers from the environment,
transporting the transporter containing the sample containers to an analytical apparatus,
placing the transporter in close proximity to a sample receiving portion of the analytical apparatus,
permitting a sample container to move directly from a storage chamber in the transporter to the receiving portion of the analytical apparatus, moving the transporter away from the analytical apparatus, after an analysis is performed, placing the transporter in close proximity to the sample receiving portion of the analytical apparatus, moving the sample container from the analytical apparatus directly into a storage chamber in the transporter, and in the transporter, isolating the sample container from the environment.

* * * * *